(12) United States Patent
MacDonald et al.

(10) Patent No.: US 8,029,190 B2
(45) Date of Patent: Oct. 4, 2011

(54) METHOD AND ARTICLES FOR SENSING RELATIVE TEMPERATURE

(75) Inventors: John Gavin MacDonald, Decatur, GA (US); Kelly D. Arehart, Roswell, GA (US); Stephanie M. Martin, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 11/801,637

(22) Filed: May 10, 2007

(65) Prior Publication Data

US 2008/0279253 A1   Nov. 13, 2008

(51) Int. Cl.
  *G01K 11/00* (2006.01)
(52) U.S. Cl. .................. 374/162; 374/159; 116/216
(58) Field of Classification Search .......... 374/159, 374/162; 116/216
  See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,600,060 A | 8/1971 | Churchill et al. |
| 3,619,254 A | 11/1971 | Davis |
| 3,692,618 A | 9/1972 | Dorschner et al. |
| 3,802,817 A | 4/1974 | Matsuki et al. |
| 3,847,139 A * | 11/1974 | Flam .............................. 600/549 |
| 3,849,241 A | 11/1974 | Butin et al. |
| 4,022,706 A | 5/1977 | Davis |
| 4,041,203 A | 8/1977 | Brock et al. |
| 4,100,324 A | 7/1978 | Anderson et al. |
| 4,323,534 A | 4/1982 | Des Marais |
| 4,340,563 A | 7/1982 | Appel et al. |
| 4,374,888 A | 2/1983 | Bornslaeger |
| 4,642,250 A * | 2/1987 | Spector .............................. 427/8 |
| 4,652,487 A | 3/1987 | Morman |
| 4,655,760 A | 4/1987 | Morman et al. |
| 4,657,802 A | 4/1987 | Morman |
| 4,663,220 A | 5/1987 | Wisneski et al. |
| 4,681,791 A * | 7/1987 | Shibahashi et al. ............. 428/96 |
| 4,720,415 A | 1/1988 | Vander Wielen et al. |
| 4,725,462 A * | 2/1988 | Kimura .......................... 428/29 |

(Continued)

FOREIGN PATENT DOCUMENTS

GB   2384556 A   7/2003

(Continued)

OTHER PUBLICATIONS

ASTM Designation: E1164-02, "Standard Practice for Obtaining Spectrometric Data for Object-Color Evaluation," Published Aug. 2002.

(Continued)

*Primary Examiner* — Lisa Caputo
*Assistant Examiner* — Mirellys Jagan
(74) *Attorney, Agent, or Firm* — Dority & Manning, P.A.

(57) ABSTRACT

A method for determining the relative body temperature of a warm-bodied animal is described. The method, in part, involves an article of manufacture that provides a manifestation, or visually observable indication on an exterior surface, of a relative state of the warm-bodied animal's body temperature, either being too cold or too hot, as a measure against relative levels of hypothermia or hyperthermia, or poor circulation.

29 Claims, 3 Drawing Sheets

COLOR TRANSITION

Where -ΔT is level of heat loss indicative of hypothermia and where color indicates to observer that skin is too cool Where ΔT is a level of heat indicative of fever or overheating and color indicates to observer that skin is too warm

U.S. PATENT DOCUMENTS

| | | | |
|---|---|---|---|
| 4,766,029 A | 8/1988 | Brock et al. | |
| 4,781,966 A | 11/1988 | Taylor | |
| 4,789,699 A | 12/1988 | Kieffer et al. | |
| 4,834,738 A | 5/1989 | Kielpikowski et al. | |
| 4,957,949 A | 9/1990 | Kamada et al. | |
| 4,965,122 A | 10/1990 | Morman | |
| 4,981,747 A | 1/1991 | Morman | |
| 5,093,422 A | 3/1992 | Himes | |
| 5,114,781 A | 5/1992 | Morman | |
| 5,116,662 A | 5/1992 | Morman | |
| 5,153,066 A * | 10/1992 | Tanaka et al. | 428/373 |
| 5,169,706 A | 12/1992 | Collier, IV et al. | |
| 5,213,881 A | 5/1993 | Timmons et al. | |
| 5,226,992 A | 7/1993 | Morman | |
| 5,272,236 A | 12/1993 | Lai et al. | |
| 5,278,272 A | 1/1994 | Lai et al. | |
| 5,284,703 A | 2/1994 | Everhart et al. | |
| 5,304,599 A | 4/1994 | Himes | |
| 5,332,613 A | 7/1994 | Taylor et al. | |
| 5,336,545 A | 8/1994 | Morman | |
| 5,350,624 A | 9/1994 | Georger et al. | |
| 5,382,400 A | 1/1995 | Pike et al. | |
| 5,385,775 A | 1/1995 | Wright | |
| 5,389,093 A * | 2/1995 | Howell | 604/361 |
| 5,414,470 A | 5/1995 | Hotta et al. | |
| 5,431,697 A | 7/1995 | Kamata et al. | |
| 5,464,688 A | 11/1995 | Timmons et al. | |
| 5,539,056 A | 7/1996 | Yang et al. | |
| 5,540,332 A | 7/1996 | Kopacz et al. | |
| 5,596,052 A | 1/1997 | Resconi et al. | |
| 5,616,201 A | 4/1997 | Finch et al. | |
| 5,649,336 A | 7/1997 | Finch et al. | |
| 5,667,635 A | 9/1997 | Win et al. | |
| 5,888,524 A | 3/1999 | Cole | |
| 6,028,018 A | 2/2000 | Amundson et al. | |
| 6,139,779 A * | 10/2000 | Small et al. | 252/583 |
| 6,323,389 B1 | 11/2001 | Thomas et al. | |
| 6,440,437 B1 | 8/2002 | Krzysik et al. | |
| 6,680,265 B1 | 1/2004 | Smith et al. | |
| 6,969,441 B2 | 11/2005 | Welch et al. | |
| 2002/0137417 A1 * | 9/2002 | Tebbe | 442/130 |
| 2003/0087566 A1 | 5/2003 | Carlyle et al. | |
| 2003/0119202 A1 | 6/2003 | Kaylor et al. | |
| 2004/0158156 A1 * | 8/2004 | Schneemeyer et al. | 600/474 |
| 2004/0237164 A1 * | 12/2004 | Aperfine et al. | 2/69 |
| 2006/0172135 A1 * | 8/2006 | Agrawal et al. | 428/411.1 |
| 2007/0142263 A1 * | 6/2007 | Stahl et al. | 510/475 |
| 2007/0252115 A1 | 11/2007 | Arehart et al. | |
| 2008/0120761 A1 * | 5/2008 | Yang et al. | 2/167 |
| 2008/0233379 A1 * | 9/2008 | O'Connor | 428/221 |
| 2009/0046760 A1 * | 2/2009 | Matheson | 374/141 |
| 2009/0143516 A1 * | 6/2009 | MacDonald et al. | 524/236 |

FOREIGN PATENT DOCUMENTS

| | | |
|---|---|---|
| GB | 2435398 | 8/2007 |
| JP | 2002363809 | 12/2002 |
| WO | WO 03/035948 | 5/2003 |

OTHER PUBLICATIONS

Japanese Industrial Standard, JIS Z8722-2000, "Methods of colour measurement—Reflecting and transmitting objects," Revised May 20, 2000.

Cost, F., Pocket Guide to Digital Printing, Delmar Publishers, Albany, NY, ISBN 0-8273-7592-1, pp. 144-145.

Mahoney, C.B. et al., "Maintaining intraoperative normothermia: A meta-analysis of outcomes with costs," *AANA Journal*, vol. 67, No. 2, Apr. 1999, pp. 155-164.

Woo, Y.J. et al., "Active Thermoregulation Improves Outcome of Off-Pump Coronary Artery Bypass," *Asian Cardiovascular & Thoracic Annals*, vol. 13, No. 2, 2005, pp. 157-160.

Patent Abstracts of Japan, JP 2002363809, publication date Dec. 18, 2002.

\* cited by examiner

FIG. 3 COLOR TRANSITION WITH PICTURE, PATTERN, OR MESSAGE

METHOD AND ARTICLES FOR SENSING RELATIVE TEMPERATURE

FIELD OF INVENTION

The present invention pertains to a method for visually indicating either the rate of temperature change or relative body temperature of a warm-blooded animal without the aide of a conventional analogue or electronic thermometer.

BACKGROUND

Thermo-regulation of mammalian bodies has been of interest for a variety of health and medical applications, as well as general consumer uses. Warm-blooded animals, including human beings, maintain thermal homeostasis. That is, they are able to keep their core body temperature within a normal range, a near constant level, regardless of the ambient temperature of the surrounding environment. This can involve not only the ability to generate heat, but also the ability to prevent being over-heated and to cool down. Body temperature maintenance incorporates a wide range of different techniques that result in a body temperature continuum. For example, typically, warm-blooded animals control their body temperature by regulating their metabolic rates (e.g. increasing their metabolic rate as the surrounding environmental temperature begins to decrease), such as through shivering when the ambient temperature becomes too cold. Additionally, when the body becomes too hot, humans perspire as another several safety features that help to regular the body's normal temperature. If the body is unable to maintain a normal temperature, hyperthermia or the opposite condition, hypothermia, can occur.

Body temperature regulation is an important parameter for patients who undergo surgery or during post operative recovery. Human body temperature can fluctuate temporarily due to various factors, such as age, physical activity, illness, or emotional stress, normal body temperature is 98.6° F. (37° C.) when the body is at rest. Studies have demonstrated that maintenance of a normal or relatively warm patient body temperature during medical procedures can minimize the likelihood of post surgical infections or other complications, and help the patient heal more quickly, thus shorten hospital stays (e.g., Woo Y J, Atluri P, Grand T J, Hsu V M, Cheung A. "Active Thermoregulation Improves Outcome of Off-Pump Coronary Artery Bypass," Asian Cardiovasc. Thorac. Ann. 2005, 13:157:160; Mahoney C B, Odom J. "Maintaining Intra-Operative Normothermia: A Meta-analysis of Outcomes with Costs. AANA J. 1999, 67:155-163). For a healthy human being, normal skin temperature around the body core is about 35° C., and the skin temperature of the arms and legs typically may range from about 31-33° C.

Regulation of an infant's body temperature is another parameter of interest for healthcare professionals, parents, and other caregivers. The normal axillary temperature of a newborn infant may range from about 36 to 37.5° C., after measuring for about 5 minutes. Because neonatal babies typically are not able to regulate their body temperature as well as older children or adults, they easily may become either cold or overheated which can lead to a variety of health problems (hypothermia, heat exhaustion, etc.). Hence, it is not wise to either cover or overdress them on warm days or underdress them on cold days. With such little skin surface, infants lose heat or overheat fast. Premature babies, in particular, are susceptible to temperature fluctuations, and are typically housed in incubators and monitored closely to ensure that they are kept sufficiently warm without overheating. A caregiver would want to know whether the infant was too cold, or at the other extreme a caregiver would wish to be able to monitor the temperature of a feverish infant. A fever temperature of 100.4° F. or greater can be dangerous and should be reported to a doctor. Similarly, the elderly are another population that may be susceptible to difficulty regulating their body temperature, especially with respect to overheating.

A temperature sensitive composition that communicates a relative response by means of a visual indicator can be incorporated into certain protective articles, clothing or garments. Nonwoven fabrics have been treated with thermochromic pigments to provide a visual indication of a shift in temperature through color change. In many cases, the thermochromic pigments are coated onto the fibers or fabric using a multi-step topical application method. However, topical application may lead to color flaws in the surface of the fabric if the coating is not uniformly applied, along with the additional cost of a post-treatment step. Certain attempts have been made to overcome this problem. U.S. Patent Application Publication No. 2003/0087566 to Carlyle, et al., for example, describes a method for uniformly incorporating a thermochromic pigment into a melt-spun fabric by incorporating it into the polymer melt at the time of fiber or filament formation. However, the method of Carlyle, et al. still lacks the desired level of control over the thermochromic characteristics of the resulting fabric in the range of ambient to body temperature.

As such, a need currently exists for an improved method of using a thermochromic material, such as a nonwoven web, fiber, or film in an application for monitoring the relative temperature of a body or its immediate ambient environment. Currently an unmet need exists for a device, method or system that can help caregivers monitor relative body temperature. Such a device or method would be a helpful and appreciated tool for either patient or child care uses.

SUMMARY OF THE INVENTION

The present invention, in part, pertains to a method for sensing relative body temperature. The method includes: a) providing at least one of the following: a garment, cover, or a protective article that is made from either a woven or nonwoven material containing a temperature sensitive dye or colorant, and b) applying the garment or protective article to a warm-blooded body.

The invention also describes a method for visually indicating relative body temperature. The method involves providing a garment or protective article that has at least two thermochromic dyes or colorants, each dye or colorant being visually reactive within a particular temperature range, placing said garment or protective article over or against a mammalian body; observing a color change in said garment or protective article, and correlating said color change with a temperature range. One of the thermochromic dye or colorant can be sensitive to a temperature within a range from about −20° C. up through about 32° C. or 33° C. to about 40° C. or 42° C. More desirably, the thermochromic dye or colorant is sensitive to a temperature within a range from about 35° C. to about 38° C. The thermochromic dye or colorant is present in combination with a visually contrasting background or component on the garment or article.

Additionally, the invention describes a method for teaching a caregiver the use of a temperature monitoring device, the method comprising: providing a body covering having imparted therein a thermochromic substance that communicates a visually detectable signal at a predetermined temperature range, In another aspect, the invention pertains to a device for monitoring a rate of temperature change of a body. The device involves using a non-electronic visual indicator to measure the relative temperature of a user's body temperature. Finally, the invention relates to an article of clothing or a protective article that has at least two layers. The article has an "inner" side, which is oriented towards or contacts a user's body and an "outer" side that is oriented away from the user's body. Each layer being adapted or tuned to a particular temperature range and can provide a visually distinct indication of relative temperature change with respect the inner and outer sides of the article. Multilayered or laminated embodiments are also envisioned.

Similarly, the invention can relate to an article of manufacture comprising a visual indicator having a thermochromic substance that changes color when exposed to a predetermined temperature or temperature range, which when worn or applied to the body of a living mammal communicates to a caregiver relative temperature differences between the mammal's core body temperature and the mammal's extremities of hands; fingers, feet, toes, or other animal counterparts. The article of manufacture can have at least two layers of dissimilar temperature sensitive dyes or colorants that are tunable for dissimilar temperature sensing values under either cold or hot conditions. The article of manufacture may exhibit a visual contrast of a ΔE value of greater than or equal to 10. The article can be a garment or protective article that provides a visually observable indication of a relative state of said mammal body temperature for either poor circulation, or relative levels of hypothermia or hyperthermia. The garment or protective article may include either a woven or nonwoven fabric, or combinations thereof, or either a stretchable or non-stretchable film, or combinations thereof. The garment or protective article may have unbonded fabric and either melt or ultrasonic bonded areas, said bonded areas change color as a function of sensing a difference in temperature relative to the rest of said unbonded fabric. In some iterations the garment or protective article has temperature sensing dyes or colorants over at least 10% of its area which is near or contacts a body.

BRIEF DESCRIPTION OF FIGURES

FIG. 3A shows an embodiment that incorporates patterns or pictures that either appear or disappear with a change in relative body or immediate ambient temperature. FIG. 3B shows an embodiment that has patterned visual contrast FIG. 3C shows an embodiment that employs alpha-numeric symbols or words as the visual indicia.

DETAILED DESCRIPTION OF THE INVENTION

Section I—Definitions

Figure 1:
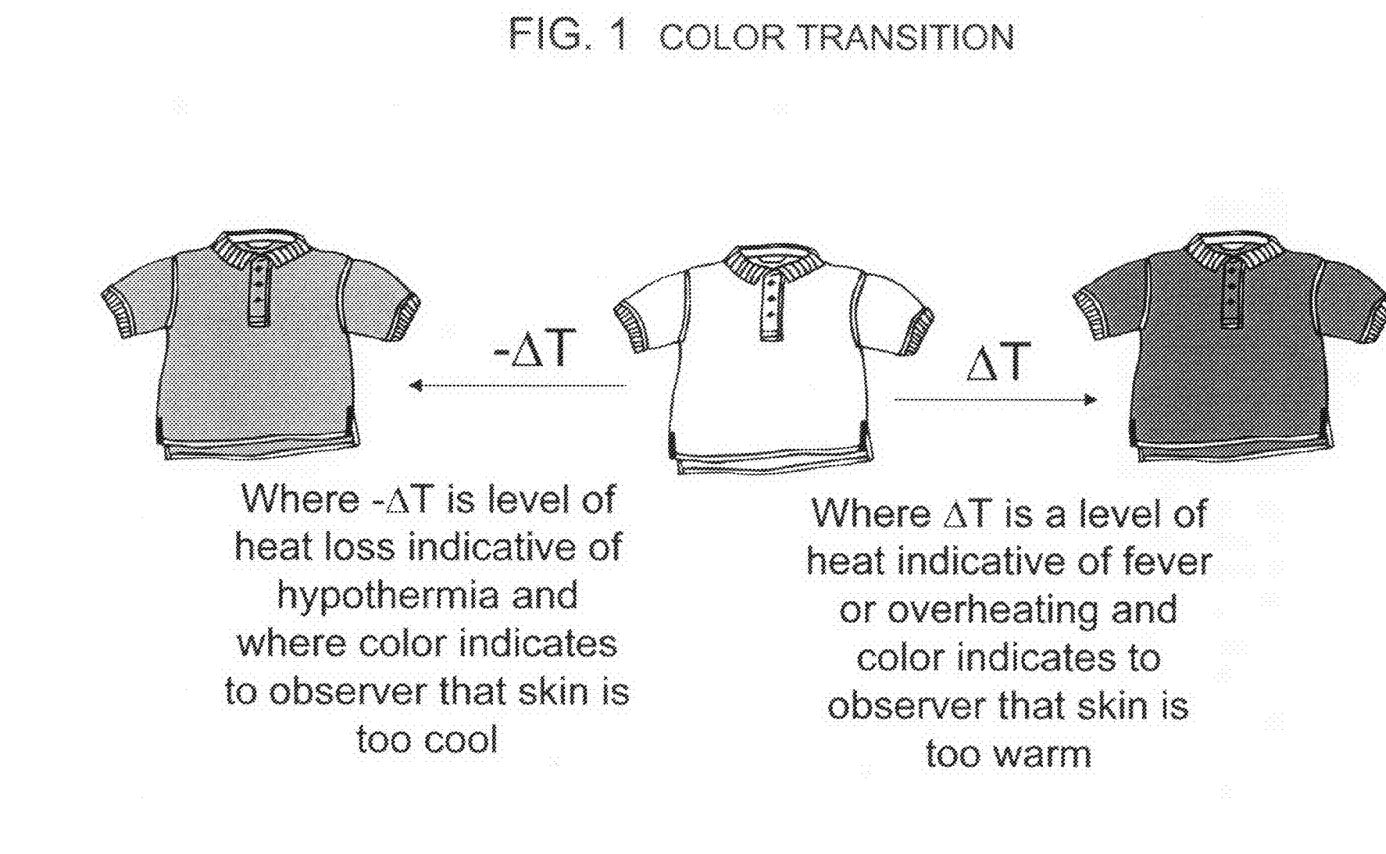
FIG. 1 is a schematic illustration of an article of clothing or covering according to the present invention that is designed to give a visually perceivable indication of a change in a user's body, skin, or immediate ambient environment. The article, as shown, is a shirt that changes color to reflect a relative change in temperature (±ΔT), where −ΔT is a level of heat loss that may result in a chill or potential hypothermia, and the color indicates to an observer that skin temperature is too cool, and where +ΔT is a level of heating that may result in either overheating or a potential fever, and the color change communicates to an observer that the skin is too warm.
Figure 2:
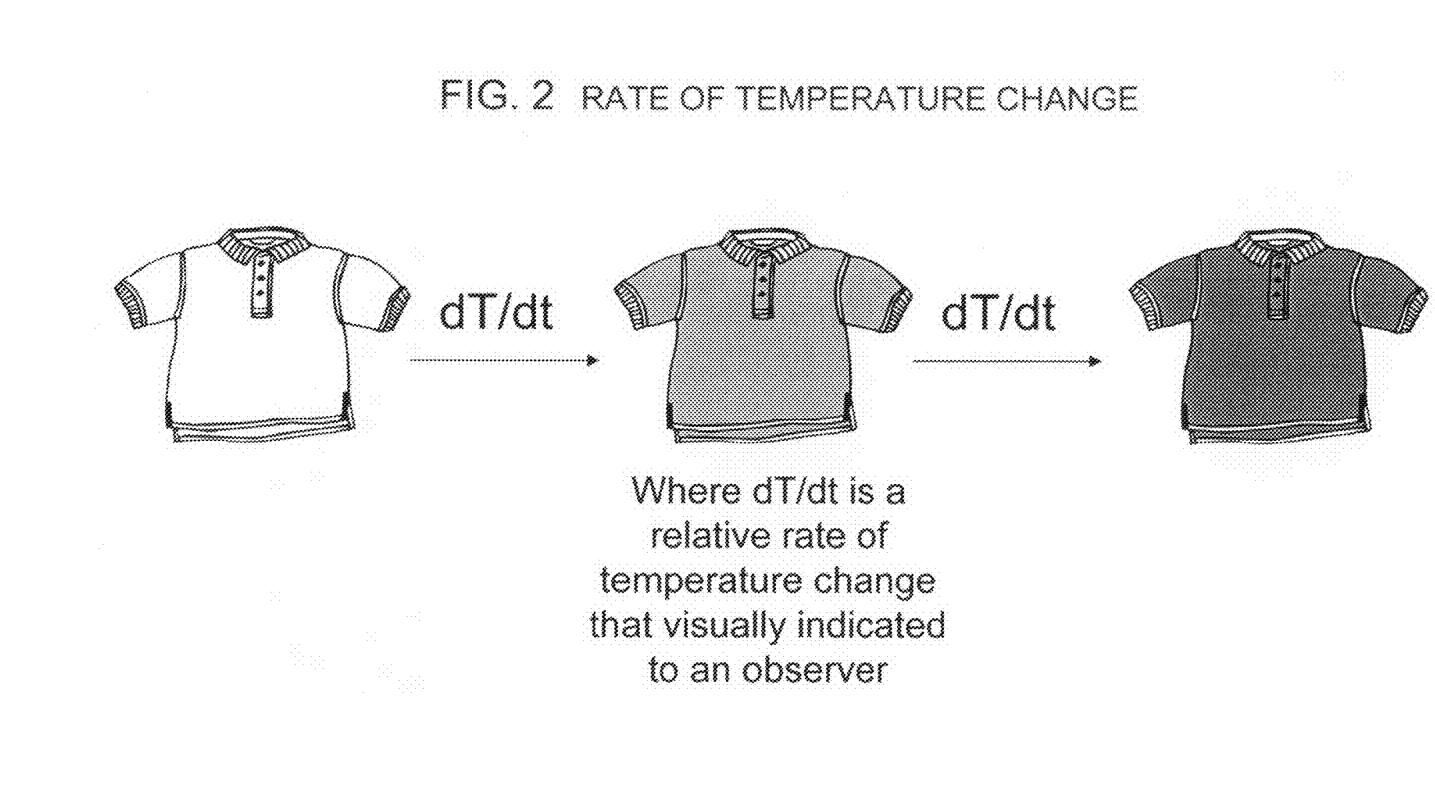
FIG. 2 is a schematic illustration of a progressive rate of change in temperature (dT/dt), either in cooling or heating, as reflected in a visually perceivable color change of an article.
Figure 3:
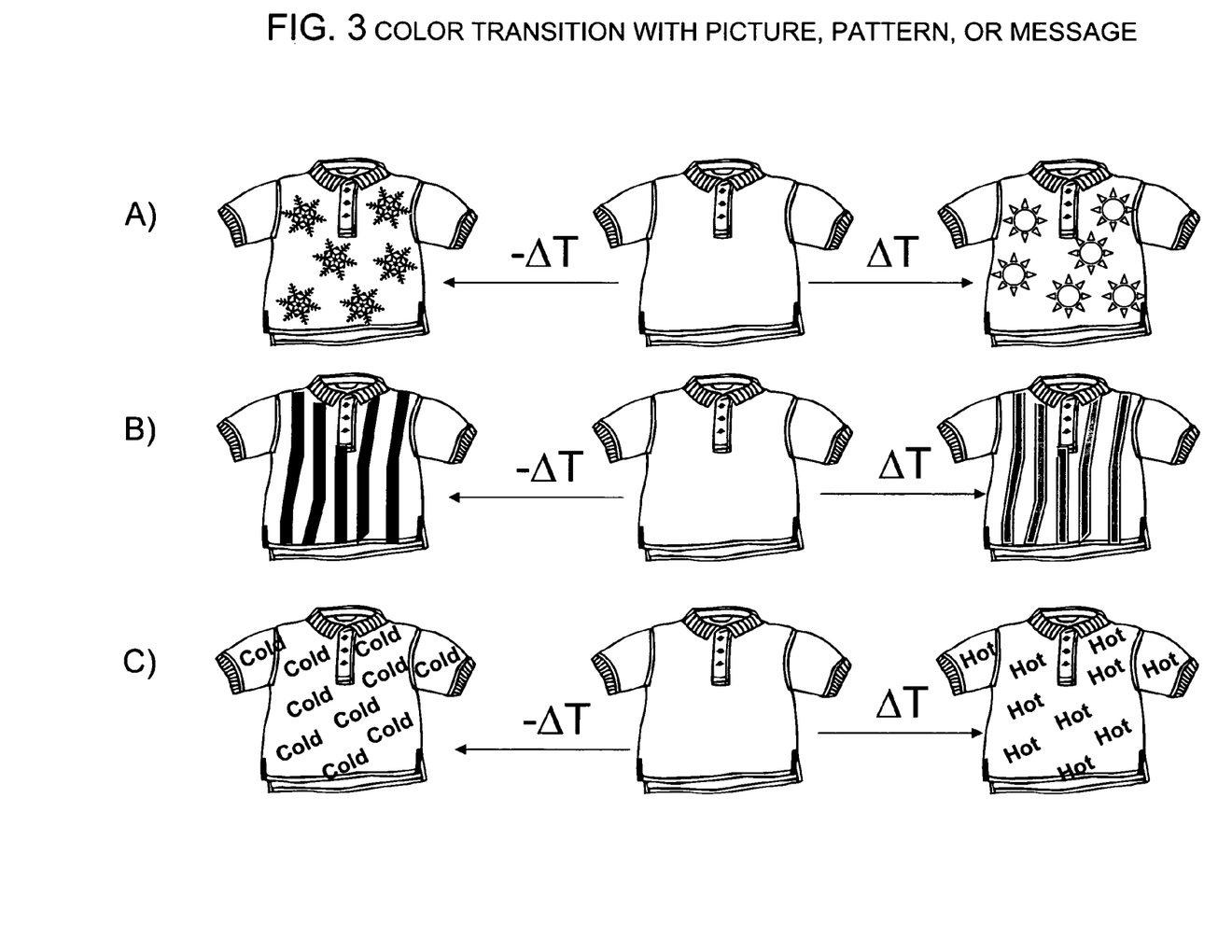
FIG. 3 illustrates alternative iterations of visually indicative designs for an article according to the present invention.

As used herein, the term "body" refers to the physical or corporal form of either a warm-blooded or mammalian animal.

As used herein, the term "body cover" or "body covering" as used herein refers to any article of clothing or protective article.

As used herein, the term "article of clothing" refers to any kind of garment or part of a garment, for example, a shirt, t-shirt, singlet, jumper suit or coverall, hat, collar, cuff, sleeve, scarf, gloves or mittens, finger gloves, underwear, pants, socks or booties, and robe or gown that is either in direct contact with the skin or hair-covered surface of a person, or may be worn one or more layers away from the immediate body surface (e.g., up to about 15 mm or 20 mm.)

As used herein, the term "protective article" refers to, for example, a blanket, drapery, wrap, bandage, sticker, or other covering that helps to insulate, monitor, or maintain body temperature for a warm-blooded animal.

As used herein, the term "fibers" generally refers to both staple length fibers and substantially continuous filaments, and likewise includes monocomponent and multicomponent fibers.

As used herein the term "nonwoven fabric or web" generally refers to a web having a structure of individual fibers or threads which are interlaid, but not in an identifiable manner as in a knitted fabric. Examples of suitable nonwoven fabrics or webs include, but are not limited to, meltblown webs, spunbond webs, bonded carded webs, coform webs, airlaid webs, etc. The basis weight of the nonwoven webs may generally vary, but is typically from about 5 grams per square meter ("gsm") to 200 gsm, in some embodiments from about 10 gsm to about 100 gsm, and in some embodiments, from about 15 gsm to about 50 gsm.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 micrometers in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502, 763 to Hartman, U.S. Pat. No. 3,502,538 to Levy, U.S. Pat.

No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 micrometers, and are often between about 5 to about 20 micrometers.

As used herein, the term "bonded carded web" refers to a web made from staple fibers that are sent through a combing or carding unit, which separates or breaks apart and aligns the staple fibers in the machine direction to form a generally machine direction-oriented fibrous nonwoven web. Such fibers are usually obtained in bales and placed in an opener/blender or picker, which separates the fibers prior to the carding unit. Once formed, the web is then bonded by one or more known methods.

As used herein, the term "airlaid web" refers to a web made from bundles of fibers having typical lengths ranging from about 3 to about 19 millimeters (mm). The fibers are separated, entrained in an air supply, and then deposited onto a forming surface, usually with the assistance of a vacuum supply. Once formed, the web is then bonded by one or more known methods.

As used herein, the term "coform web" generally refers to a composite material containing a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes.

As used herein, the term "elastomeric" or "elastic" refers to a material that, upon application of a stretching force, is stretchable in at least one direction (such as the CD direction), and which upon release of the stretching force, contracts/returns to approximately its original dimension. For example, a stretched material may have a stretched length that is at least 50% greater than its relaxed unstretched length, and which will recover to within at least 50% of its stretched length upon release of the stretching force. A hypothetical example would be a one (1) inch sample of a material that is stretchable to at least 1.50 inches and which, upon release of the stretching force, will recover to a length of not more than 1.25 inches. The elastomeric sheet contracts or recovers, desirably, at least 50%, and even more desirably, at least 80% of the stretch length in the cross machine direction.

Section II—Description

Given the importance of monitoring body temperature of the elderly, infants, and patients for medical procedures, the present invention provides a caregiver an objective visual means to help regulate an individual's body temperature. The present invention involves an innovative method for sensing relative body temperature. The method entails providing or using at least one of the following: a protective article or garment which change color when exposed to a source of heating or cooling; and applying the garment or protective article to a warm-blooded body to visually indicate relative body temperature or a rate of change in body temperature. The garment or protective article is made from either a woven or nonwoven material containing a temperature sensitive dye or colorant. When adapted to be sensitive to a predetermined temperature range, such as normal human body temperature, the present invention visually indicate to a caregiver whether the ambient environment immediately proximate to an individual's body (e.g., an infant, child, elderly, or non-verbal patient), is either overheating or being cooled excessively or too rapidly.

Another use or function the present invention can be used for is to ascertain whether either a heating or cooling device (e.g., heating pad or ice pack) is working properly at a suitable temperature or temperature range (i.e., not too hot or too cold). A temperature indicator can provide information to allow a user or caregiver to observe the temperature and moderate it for comfort and safety. For instance, it can prevent the introducing a sudden cold to a body and protect a patient from experiencing cold shock when a ice pack is applied to the skin by monitoring the relative cooling effect, for instance, when integrated as part of an exterior cover or sleeve. In another instance, a caregiver can monitor that a premature infant never has a body temperature of less than about 36° C.

According to the present inventive methods, protective articles or articles of clothing can be placed either directly adjacent or proximal to the surface of the body. That is, within about two or three layers of clothing, such that the first layer of clothing is in direct or immediately contact with the body or skin. The thermochromic material can be arranged to exhibit different functions on two opposing sides. For instance, articles that have at least two layers can be adapted to monitor and communicate a visual cue to the temperature of the body as well as immediate ambient temperature immediately adjacent to the body. According to the principles of thermodynamics, heat diffusion in air or water fluid, water vapor in air, one can sense both the body temperature as well as the environmental surrounding the body. Although some embodiments may use a single color change for the garment or protective article, additional resins potentially can be incorporated into the nonwoven substrate which would permit one to "fine tune" the article for particular uses at specific temperature ranges. For instance, one may incorporate different zones or range of several temperature sensitivity (e.g., "too cool," "warm enough" and "too warm") indicator mechanisms in a single garment article. It is desirable that the garment or article exhibit a high visual contrast relative to a background and a color change or $\Delta E$ value.

Garments and Articles

Multiple layered garments or protective articles can have each layer be sensitive to a different temperature range. A protective article or garment can have two sides with different themochromic dyes or colorants, each adapted to be sensitive to color a particular range of temperatures. One side, for instance, may be adapted to heat and an opposing side to cold. With such a configuration, according to an embodiment, one can simultaneously sense a wearer or user's body temperature as well as the relative air temperature surrounding the body, immediately above the surface of protective article or garment, such as up to about 24 mm from the surface. Detected by the principles of thermodynamic heat diffusion, whether in a liquid or gaseous fluid environment, such as water, air, or water vapor pressure. The method for visually indicating relative body temperature can include: providing a garment or protective article that has at least two thermochromic dyes or colorants, each dye or colorant being visually reactive within a particular temperature range; placing said garment or protective article over or against a mammalian body; observing a color change in said garment or protective article; and correlating the color change with a temperature range. This process can provide a quick, convenient visual signal to an observer of the relative body temperature in the absence of conventional thermometers. At least one of the thermochromic dye or colorant can be sensitive to a temperature within a wide a range or over ranges. For instance, in a low temperature range from about −20° C. or −15° C. up to about 10° C. or 20° C. Alternatively, the thermochromic polymer is sensitive in a temperature range from about 0° C. to about 25° C. or 27° C., or yet another from about 30° C. to about 40° C. Desirably, at least one of the thermochromic dye or colorant is sensitive to a temperature within a range from about 32° C. or 34° C. to about 38° C. The thermochromic dye or colorant can be present in combination with non-temperature sensitive dyes or colorants. According to another embodiment, the present invention relates to a device of monitoring a rate of temperature change of a body that involves using a non-electronic visual indicator. The device can operate according to the method above. To suit a predetermined function or achieve a desired end-user's purposes, one can select from a variety of material types for their color contrast and tune their respective sensitivity to an appropriate temperature range. Caregiver, either a typical consumer at home or skilled nursing professional, can use the present method and articles with ease. Depending on the specific intended use and/or particular parameters, a protective article or article of clothing can adapted or adjusted to be sensitive over a variety of temperature ranges, when providing a visual indication of relative temperature. For example, an insulating blanket or so-called "onesie" suit or jacket for infants (especially pre-mature babies) can be designed to change color and visually indicate whether the infant's body temperature drops below about 36° C. or 37° C., or whether the baby becomes too warm.

The invention also encompasses a method for teaching a caregiver the use of a temperature monitoring device, the method comprising: providing a body covering having imparted therein a thermochromic substance that communicates a visually detectable signal at a predetermined temperature range, and exhibits an observable color change of a ΔE value greater than three (>3); contacting the body covering to a warm-blooded body; monitoring for a visual change in the body covering; and providing an instruction to the caregiver to follow the method.

To characterize the observed color changes objectively when monitoring relative temperature about rather than limit the invention to specific combinations of high contrast to address synergy, the present invention can be characterized using observations of color manifestation. For example, rather than say that a color change from red to yellow or the reverse might be preferred, it may be more meaningful to speak in terms of a ΔE value that signifies an easily observable color change. Subtle or slight distinctions in shades or hues of color can be difficult to detect. For a trained observer, color distinctions are detectable to a naked eye at a threshold ΔE value of about 3. For a more common observer, visual difference or changes in color become detectable at ΔE value of about 5. Hence, the optical or colored indicative mechanism according to the present invention exhibits a ΔE value greater than three (>3), desirably greater than or equal to five (≧5), and more desirably greater than or equal to ten (≧10). In some embodiments, the ΔE values can range from about 12 or 15 to about 80 or 85, inclusive. Typically, articles that are used to express the present temperature monitoring method exhibit ΔE values of about 20 or greater. In preferred embodiments, the ΔE value can range from about 40 or 50 to about 60 or 65, for a medium to relatively high level of color contrast.

As an example, a yellow-pink combination had the highest ΔE, but all of the color changes measured would be easily visible to the naked eye of an untrained observer.

TABLE I

Delta E for Various Matsui Chromicolor Combinations

| | L* | A* | B* | Delta E |
|---|---|---|---|---|
| A1 (New Fast Yellow) | 90.42 | −13.75 | 90.55 | 19.88616 |
| E1 (Pink) | 45.56 | 48.85 | 21.23 | 114.5032 |
| I1 (Brilliant Green) | 50.25 | −58.07 | 19.32 | 84.83576 |
| B1 (Gold Orange) | 62.99 | 53.91 | 56.96 | 95.91618 |
| Blank (#1 Yellow) | 97.62 | −31.23 | 84.38 | |

In many cases, colored inks are available in a certain temperature transition range in numerous colors (e.g. Matsui products). Thus, according to the present invention various thermo-chromographic dyes that have transitions in the physiological range of importance (such as about 30-42° C.) may be incorporated for use in temperature monitoring garments or protective articles. Examples of some specific dyes with specific transition temperatures may include those such as listed in Table I, above. In comparison to leuco dyes, liquid crystalline dyes appear to exhibit greater temperature sensitivity, hence generating a relatively faster reaction time, or "tighter" transition in color in the predetermined temperature ranges of interest, which is another option for monitoring temperature rate of change.

Total Color Change Value: ΔE Color Measurement

In measuring color, a person certainly can evaluate the relative shades and hues of color by means of comparison using the naked eye. For an objective standard, however, a method of evaluation that provides the observer with numerical data along with a process to quantify that data is needed using a spectrophotometer, and a color interpretation method: Delta-E (ΔE). Color intensity and change may be measured using a conventional test known as "CIELAB", which is discussed in *Pocket Guide to Digital Printing* by F. Cost, Delmar Publishers, Albany, N.Y. ISBN 0-8273-7592-1, at pages 144 and 145, the contents of which are incorporated herein by reference. This method defines-three variables, L*, a*, and b*, which correspond to three characteristics of a perceived color based on the opponent theory of color perception. The three variables have the following meaning:

L*=Lightness (or luminosity), ranging from 0 to 100, where 0=dark and 100=light;

a*=Red/green axis, ranging approximately from −100 to 100; positive values are reddish and negative values are greenish; and b*=Yellow/blue axis, ranging approximately from −100 to 100; positive values are yellowish and negative values are bluish.

Because CIELAB color space is somewhat visually uniform, a single number may be calculated that represents the difference between two colors as perceived by a human. This difference is termed ΔE and calculated by taking the square root of the sum of the squares of the three differences (ΔL*, Δa*, and Δb*) between the two colors.

In CIELAB color space, each ΔE unit is approximately equal to a "just noticeable" difference between two colors. CIELAB is therefore a good measure for an objective device-independent color specification system that may be used as a reference color space for the purpose of color management and expression of changes in color: Using this test, color intensities (L*, a*, and b*) may thus be measured using, for instance, a handheld spectrophotometer from Minolta Co. Ltd. of Osaka, Japan (Model #CM2600d). This instrument utilizes the D/8 geometry conforming to CIE No. 15, ISO 7724/1, ASTME1164 and JIS Z8722-1982 (diffused illumination/8-degree viewing system. The D65 light reflected by the specimen surface at an angle of 8 degrees to the normal of the surface is received by the specimen-measuring optical system. Still other suitable devices for measuring the intensity of a visual color may also be used in the present invention. For example, a suitable reflectance reader is described in U.S. Patent App. Pub. No. 2003/0119202 to Kaylor, et al., the content of which is incorporated herein in by reference.

Materials

Generally speaking, the present invention can be achieved through the creative use of a melt-extrudable composition that includes a thermochromic substance. The melt-extrudable composition may be formed into a material (e.g., film, fiber, or nonwoven web) exhibiting thermochromic properties. As used herein, the term "thermochromic" refers to a material that undergoes a color change at an activation temperature. That is, the material changes from one color to another color, from no color to a color, or from a color to no color at the activation temperature. In accordance with the present invention, the activation temperature at which the color change occurs is typically between room temperature (i.e., about 25° C.) and body temperature (e.g., about 40° C.) so that the material exhibits a certain color at room temperature and another color upon contact with human skin or other parts of the body, etc. For example, the activation temperature may be from about 30° C. to about 40° C., and in some embodiments, from about 35° C. to about 38° C. If desired, the thermochromic substance may also undergo a series of subsequent color changes with a further increase in temperature above the initial activation temperature.

Any thermochromic substance that undergoes a color change at the desired temperature may generally be employed in the present invention. For example, liquid crystals may be employed as a thermochromic substance in some embodiments. The wavelength of light ("color") reflected by liquid crystals depends in part on the pitch of the helical structure of the liquid crystal molecules. Because the length of this pitch varies with temperature, the color of the liquid crystals is also a function of temperature. One particular type of liquid crystal that may be used in the present invention is a liquid crystal cholesterol derivative. Exemplary liquid crystal cholesterol derivatives may include alkanoic and aralkanoic acid esters of cholesterol, alkyl esters of cholesterol carbonate, cholesterol chloride, cholesterol bromide, cholesterol acetate, cholesterol oleate, cholesterol caprylate, cholesterol oleyl-carbonate, and so forth. Other suitable liquid crystal cholesterol derivatives are described in U.S. Pat. No. 3,600,060 to Churchill, et al.; U.S. Pat. No. 3,619,254 to Davis; and U.S. Pat. No. 4,022,706 to Davis, which are incorporated herein in their entirety by reference thereto for all purposes.

In addition to liquid crystals, another suitable thermochromic substance that may be employed in the present invention includes a proton accepting chromgen ("Lewis base") and a solvent. The melting point of the solvent controls the temperature at which the chromogen will change color. More specifically, at a temperature below the melting point of the solvent, the chromogen generally possesses a first color (e.g., white). When the solvent is heated to its melting temperature, the chromogen becomes protonated, thereby resulting in a shift of the absorption maxima of the chromogen towards either the red ("bathochromic shift") or blue end of the spectrum ("hypsochromic shift"). The nature of the color change depends on a variety of factors, include the type of proton-accepting chromogen utilized and the presence of any additional temperature-insensitive chromogens. Regardless, the color change is typically reversible in that the chromogen deprotonates when cooled.

Although not required, the proton-accepting chromogen is typically an organic dye, such as a leuco dye. In solution, the protonated form of the leuco dye predominates at acidic pH levels (e.g., pH of about 4 or less). When the solution is made more alkaline through protonation, however, a color change occurs. Of course, the position of this equilibrium may be shifted with temperature when other components are present. Suitable leuco dyes for use in the present invention may include, for instance, phthalides; phthalanes; substituted phthalides or phthalanes, such as triphenylmethane phthalides, triphenylmethanes, or diphenylmethanes; acyl-leucomethylene blue compounds; fluoranes; indolylphthalides, spiropyranes; cumarins; and so forth. Exemplary fluoranes include, for instance, 3,3'-dimethoxyfluorane, 3,6-dimethoxyfluorane, 3,6-di-butoxyfluorane, 3-chloro-6-phenylamino-flourane, 3-diethylamino-6-dimethylfluorane, 3-diethylamino-6-methyl-7-chlorofluorane, and 3-diethyl-7, 8-benzofluorane, 3,3'-bis(p-dimethyl-aminophenyl)-7-phenylaminofluorane, 3-diethylamino-6-methyl-7-phenylamino-fluorane, 3-diethylamino-7-phenyl-aminofluorane, and 2-anilino-3-methyl-6-diethylamino-fluorane. Likewise, exemplary phthalides include 3,3',3"-tris(p-dimethylaminophenyl)phthalide, 3,3'-bis(p-dimethyl-aminophenyl)phthalide, 3,3-bis(p-diethylamino-phenyl)-6-dimethylamino-phthalide, 3-(4-diethylaminophenyl)-3-(1-ethyl-2-methylindol-3-yl)phthalide, and 3-(4diethylamino-2-methyl)phenyl-3-(1,2-dimethylindol-3-yl)phthalide.

Although any solvent may generally be employed in the present invention, it is typically desired that the solvent have a low volatility. For example, the solvent may have a boiling point of about 150° C. or higher, and in some embodiments, from about 170° C. to 280° C. Likewise, the melting temperature of the solvent is also typically from about 25° C. to about 40° C., and in some embodiments, from about 30° C. to about 37° C. Examples of suitable solvents may include saturated or unsaturated alcohols containing about 6 to 30 carbon atoms, such as octyl alcohol, dodecyl alcohol, lauryl alcohol, cetyl alcohol, myristyl alcohol, stearyl alcohol, behenyl alcohol, geraniol, etc.; esters of saturated or unsaturated alcohols containing about 6 to 30 carbon atoms, such as butyl stearate, lauryl laurate, lauryl stearate, stearyl laurate, methyl myristate, decyl myristate, lauryl myristate, butyl stearate, lauryl palmitate, decyl palmitate, palmitic acid glyceride, etc.; azomethines, such as benzylideneaniline, benzylidenelaurylamide, o-methoxybenzylidene laurylamine, benzylidene p-toluidine, p-cumylbenzylidene, etc.; amides, such as acetamide, stearamide, etc.; and so forth.

The thermochromic substance may also include a proton-donating agent (also referred to as a "color developer") to facilitate the reversibility of the color change. Such proton-donating agents may include, for instance, phenols, azoles, organic acids, esters of organic acids, and salts of organic acids. Exemplary phenols may include phenylphenol, bisphenol A, cresol, resorcinol, chlorolucinol, β-naphthol, 1,5-dihydroxynaphthalene, pyrocatechol, pyrogallol, trimer of p-chlorophenol-formaldehyde condensate, etc. Exemplary azoles may include benzotriaoles, such as 5-chlorobenzotriazole, 4-laurylaminosulfobenzotriazole, 5-butylbenzotriazole, dibenzotriazole, 2-oxybenzotriazole, 5-ethoxycarbonylbenzotriazole, etc.; imidazoles, such as oxybenzimidazole, etc.; tetrazoles; and so forth. Exemplary organic acids may include aromatic carboxylic acids, such as salicylic acid, methylenebissalicylic acid, resorcylic acid, gallic acid, benzoic acid, p-oxybenzoic acid, pyromellitic acid, β-naphthoic acid, tannic acid, toluic acid, trimellitic acid, phthalic acid, terephthalic acid, anthranilic acid, etc.; aliphatic carboxylic acids, such as stearic acid, 1,2-hydroxystearic acid, tartaric acid, citric acid, oxalic acid, lauric acid, etc.; and so forth. Exemplary esters may include alkyl esters of aromatic carboxylic acids in which the alkyl moiety has 1 to 6 carbon atoms, such as butyl gallate, ethyl p-hydroxybenzoate, methyl salicylate, etc.

The amount of the proton-accepting chromogen employed may generally vary, but is typically from about 2 wt. % to about 20 wt. %, and in some embodiments, from about 5 to about 15 wt. % of the thermochromic substance. Likewise, the proton-donating agent may constitute from about 5 to about 40 wt. %, and in some embodiments, from about 10 wt. % to about 30 wt. % of the thermochromic substance. In addition, the solvent may constitute from about 50 wt. % to about 95 wt. %, and in some embodiments, from about 65 wt. % to about 85 wt. % of the thermochromic substance.

If desired, the above-described components may also be encapsulated to enhance the stability of the thermochromic substance during processing. For example, the chromogen, solvent, and other components may be mixed with a thermosetting resin according to any conventional method, such as interfacial polymerization, in-situ polymerization, etc. The thermosetting resin may include, for example, polyester resins, polyurethane resins, melamine resins, epoxy resins, diallyl phthalate resins, vinylester resins, and so forth. The resulting mixture may then be granulated and optionally coated with a hydrophilic macromolecular compound, such as alginic acid and salts thereof, carrageenan, pectin, gelatin and the like, semisynthetic macromolecular compounds such as methylcellulose, cationized starch, carboxymethylcellulose, carboxymethylated starch, vinyl polymers (e.g., polyvinyl alcohol), polyvinylpyrrolidone, polyacrylic acid, polyacrylamide, maleic acid copolymers, and so forth. The resulting capsules typically have a size of from about 1 to about 50 micrometers, and in some embodiments, from about 3 to about 15 micrometers. Various other suitable encapsulation techniques are also described in U.S. Pat. No. 4,957,949 to Kamada, et al. and U.S. Pat. No. 5,431,697 to Kamata, et al., which are incorporated herein in their entirety by reference thereto for all purposes. Commercially available encapsulated thermochromic substances may be obtained from Matsui Shikiso Chemical Co., Ltd. of Kyoto, Japan under the designation "Chromicolor" (e.g., Deep Blue Type #37 or Red E-1 Type #37).

In accordance with the present invention, the thermochromic substance is compounded with a melt-extrudable thermoplastic composition for use in the formation of a film, fiber, or nonwoven web. Although not required, the thermochromic substance may be pre-blended with a carrier resin to form a masterbatch that is compatible with the thermoplastic composition. Without intending to be limited by theory, the present inventors believe that the thermochromic substance may be more miscible with amorphous regions of a polymer than the crystalline regions. Thus, the carrier resin may be generally amorphous or semicrystalline to optimize compatibility with the thermochromic substance. The amorphous state is considered to be a randomly tangled mass of polymer chains. Amorphous polymers may have an X-ray diffraction pattern of a diffuse halo, which indicates no regularity in the polymer structure. Amorphous polymers also show softening behaviors at the glass transition temperature, but no true melt or first order transition. The semicrystalline state of polymers is one in which long segments of the polymer chains appear in both amorphous and crystalline states or phases. The crystalline phase contains multiple lattices in which the polymer chain assumes a chain-folded conformation (lamellae) in which there is a highly ordered registry in adjacent folds of the various chemical moieties of which the chain is constructed. The packing arrangement (short order orientation) within the lattice is highly regular in both its chemical and geometric aspects. Semicrystalline polymers show characteristic melting points, above which the crystalline lattices become disordered and rapidly lose their identity. Either concentric rings or a symmetrical array of spots, which are indicative of the nature of the crystalline order, generally distinguishes the X-ray diffraction pattern of semicrystalline polymers (or copolymers).

Exemplary amorphous polymers include polystyrene, polycarbonate, acrylic, acrylonitrile-butadiene-styrene (ABS), styrene-acrylonitrile, and polysulfone. Exemplary semicrystalline polymers include high and low density polyethylene, polypropylene, polyoxymethylene, poly(vinylidine fluoride), poly(methyl pentene), poly(ethylene-chlorotrifluoroethylene), poly(vinyl fluoride), poly(ethylene oxide), poly(ethylene terephthalate), poly(butylene terephthalate), nylon 6, nylon 66, poly(vinyl alcohol) and polybutene. Particularly desired semicrystalline polymers are predominantly linear polymers having a regular structure. Examples of semi-crystalline, linear polymers that may be used in the present invention include polyethylene, polypropylene, blends of such polymers and copolymers of such polymers. Semi-crystalline polyethylene-based polymers, for instance, may have a melt index of greater than about 5 grams per 10 minutes, and in some embodiments, greater than about 10 grams per 10 minutes (Condition E at 190° C., 2.16 kg), as well as a density of greater than about 0.910 grams per cubic centimeter ($g/cm^3$), in some embodiments greater than about 0.915 $g/cm^3$, in some embodiments from about 0.915 to about 0.960 $g/cm^3$, in some embodiments from about 0.917 and 0.960 $g/cm^3$. Likewise, semi-crystalline polypropylene-based polymers may have a melt index of greater than about 10 grams per 10 minutes, and in some embodiments, greater than about 20 grams per 10 minutes, as well as a density of from about 0.89 to about 0.90 $g/cm^3$. Specific examples of such polymers include ExxonMobil 3155, Dow polyethylenes such as DOWLEX™ 2517; Dow LLDPE DNDA-1082, Dow LLDPE DNDB-1077, Dow LLDPE 1081, and Dow LLDPE DNDA 7147. In some instances, higher density polymers may be useful, such as Dow HDPE DMDA-8980. Additional resins include Escorene™ LL 5100 and Escorene™ LL 6201 from ExxonMobil. Polypropylene-based resins having a density of from about 0.89 $g/cm^3$ to about 0.90 $g/cm^3$ may also be used, such as homopolymers and random copolymers such as ExxonMobil PP3155, PP1074KN, PP9074MED and Dow 6D43.

The amount of the carrier resin employed will generally depend on a variety of factors, such as the type of carrier resin and thermoplastic composition, the type of thermochromic substance, the processing conditions, etc. Typically, the carrier resin constitutes from about 10 wt. % to about 80 wt. %, in some embodiments from about 20 wt. % to about 70 wt. %, and in some embodiments, from about 40 wt. % to about 60 wt. % of the masterbatch. The thermochromic substance likewise normally constitutes from about 10 wt. % to about 80 wt. %, in some embodiments from about 20 wt. % to about 70 wt. %, and in some embodiments, from about 40 wt. % to about 60 wt. % of the masterbatch.

The carrier resin may be blended with the thermochromic substance using any known technique, such as batch and/or continuous compounding techniques that employ, for example, a Banbury mixer, Farrel continuous mixer, single screw extruder, twin screw extruder, etc. If desired, the carrier resin and thermochromic substance may be dry blended, i.e., without a solvent. After blending, the masterbatch may be processed immediately or compression molded into pellets for subsequent use. One suitable compression molding device is a die and roller type pellet mill. Specifically, the masterbatch (in granular form) is fed continuously to a pelletizing cavity. The masterbatch is compressed between a die and rollers of the cavity and forced through holes in the die. As pellets of the composition are extruded, a knife or other suitable cutting surface may shear the pellets into the desired size.

Regardless of whether the thermochromic substance is pre-blended with a carrier resin, it is ultimately compounded with a melt-extrudable thermoplastic composition to form a film, fiber, or nonwoven web. The thermochromic substance or masterbatch containing the substance may be miscible with the thermoplastic composition. Otherwise, the components may simply be blended under high shear or modified to improve their interfacial properties. The thermochromic substance may be blended with the thermoplastic composition (e.g., polypropylene or polyethylene) before melt extrusion or within the extrusion apparatus itself. The thermochromic substance may constitute from about 0.001 wt. % to about 10 wt. %, in some embodiments from about 0.01 wt. % to about 5 wt. %, and in some embodiments, from about 0.1 wt. % to about 1 wt. % of the blend.

Exemplary melt-extrudable polymers suitable for use in the thermoplastic composition may include, for example, polyolefins, polyesters, polyamides, polycarbonates, copolymers and blends thereof, etc. Suitable polyolefins include polyethylene, such as high density polyethylene, medium density polyethylene, low density polyethylene, and linear low density polyethylene; polypropylene, such as isotactic polypropylene, atactic polypropylene, and syndiotactic polypropylene; polybutylene, such as poly(1-butene) and poly(2-butene); polypentene, such as poly(1-pentene) and poly(2-pentene); poly(3-methyl-1-pentene); poly(4-methyl-1-pentene); and copolymers and blends thereof. Suitable copolymers include random and block copolymers prepared from two or more different unsaturated olefin monomers, such as ethylene/propylene and ethylene/butylene copolymers. Suitable polyamides include nylon 6, nylon 6/6, nylon 4/6, nylon 11, nylon 12, nylon 6/10, nylon 6/12, nylon 12/12, copolymers of caprolactam and alkylene oxide diamine, etc., as well as blends and copolymers thereof. Suitable polyesters include poly(lactide) and poly(lactic acid) polymers as well as polyethylene terephthalate, polybutylene terephthalate, polytetramethylene terephthalate, polycyclohexylene-1,4-dimethylene terephthalate, and isophthalate copolymers thereof, as well as blends thereof.

If desired, elastomeric polymers may also be used in the thermoplastic composition, such as elastomeric polyesters, elastomeric polyurethanes, elastomeric polyamides, elastomeric polyolefins, elastomeric copolymers, and so forth. Examples of elastomeric copolymers include block copolymers having the general formula A-B-A' or A-B, wherein A and A' are each a thermoplastic polymer endblock that contains a styrenic moiety and B is an elastomeric polymer midblock, such as a conjugated diene or a lower alkene polymer. Such copolymers may include, for instance, styrene-isoprene-styrene (S-I-S), styrene-butadiene-styrene (S-B-S), styrene-ethylene-butylene-styrene (S-EB-S), styrene-isoprene (S-I), styrene-butadiene (S-B), and so forth. Commercially available A-B-A' and A-B-A-B copolymers include several different S-EB-S formulations from Kraton Polymers of Houston, Tex. under the trade designation KRATON®. KRATON® block copolymers are available in several different formulations, a number of which are identified in U.S. Pat. Nos. 4,663,220, 4,323,534, 4,834,738, 5,093,422 and 5,304,599, which are hereby incorporated in their entirety by reference thereto for all purposes. Other commercially available block copolymers include the S-EP-S elastomeric copolymers available from Kuraray Company, Ltd. of Okayama, Japan, under the trade designation SEPTON®. Still other suitable copolymers include the S-I-S and S-B-S elastomeric copolymers available from Dexco Polymers of Houston, Tex. under the trade designation VECTOR®. Also suitable are polymers composed of an A-B-A-B tetrablock copolymer, such as discussed in U.S. Pat. No. 5,332,613 to Taylor. et al., which is incorporated herein in its entirety by reference thereto for all purposes. An example of such a tetrablock copolymer is a styrene-poly(ethylene-propylene)-styrene-poly(ethylene-propylene) ("S-EP-S-EP") block copolymer.

Examples of elastomeric polyolefins include ultra-low density elastomeric polypropylenes and polyethylenes, such as those produced by "single-site" or "metallocene" catalysis methods. Such elastomeric olefin polymers are commercially available from ExxonMobil Chemical Co. of Houston, Tex. under the trade designations ACHIEVE® (propylene-based), EXACT® (ethylene-based), and EXCEED® (ethylene-based). Elastomeric olefin polymers are also commercially available from DuPont Dow Elastomers, LLC (a joint venture between DuPont and the Dow Chemical Co.) under the trade designation ENGAGE® (ethylene-based) and from Dow Chemical Co. of Midland, Mich. under the name AFFINITY® (ethylene-based). Examples of such polymers are also described in U.S. Pat. Nos. 5,278,272 and 5,272,236 to Lai, et al., which are incorporated herein in their entirety by reference thereto for all purposes. Also useful are certain elastomeric polypropylenes, such as described in U.S. Pat. No. 5,539,056 to Yang, et al. and U.S. Pat. No. 5,596,052 to Resconi. et al., which are incorporated herein in their entirety by reference thereto for all purposes.

Once formed, the resulting melt-extrudable blend may then be extruded through a die. Although the die may have any desired configuration, it typically contains a plurality of orifices arranged in one or more rows extending the full width of the machine. The orifices may be circular or noncircular in cross-section. As stated above, the extruded blend may be formed into a thermochromic film in some embodiments of the present invention. Any known technique may be used to form a film from the thermochromic substance, including blowing, casting, flat die extruding, etc. For example, a thermochromic film may be formed by melt extruding the blend, immediately chilling the extruded material (e.g., on a chilled roll) to form a precursor film, and optionally orienting the precursor film in the machine direction, cross machine direction, or both. Alternatively, thermochromic fibers may also be formed according to the present invention. Such fibers may be formed by melt extruding the blend, attenuating the extruded material, and collecting the fibers on a roll (e.g., godet roll) for direct use or on a moving foraminous surface to form a thermochromic nonwoven web.

Upon formation, the thermochromic material (e.g., film, fiber, or nonwoven web) may be used in a wide variety of applications. For example, the thermochromic material may be incorporated into a "medical product", such as surgical gowns, surgical drapes, facemasks, head coverings, surgical caps, shoe coverings, sterilization wraps, surgical gloves, dilatation balloons, inflatable cuffs, external catheters, catheter balloons, instrument covers, warming blankets, heating pads, and so forth. In one embodiment, the thermochromic material of the present invention is used to form one or more layers of a barrier fabric of a medical product. Barrier fabrics may, for instance, contain a nonwoven laminate, such as a spunbond/meltblown/spunbond (SMS) laminate and/or a spunbond/meltblown (SM) laminate. Various examples of SMS laminates are described in U.S. Pat. No. 4,041,203 to Brock et al.; U.S. Pat. No. 5,213,881 to Timmons, et al.; U.S. Pat. No. 5,464,688 to Timmons et al.; U.S. Pat. No. 4,374,888 to Bornslaeger; U.S. Pat. No. 5,169,706 to Collier, et al.; and U.S. Pat. No. 4,766,029 to Brock et al., which are incorporated herein in their entirety by reference thereto for all purposes. Commercially available SMS laminates may be obtained from Kimberly-Clark Corporation under the designations Spunguard® and Evolution®. If desired, the thermochromic material may form the spunbond and/or meltblown layers of the nonwoven laminates.

Of course, the thermochromic material may also be used in various other articles. For example, the thermochromic material may be incorporated into an "absorbent article" that is capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, mitt wipe, and so forth; medical absorbent articles, such as garments, fenestration materials, underpads, bedpads, bandages, absorbent drapes, and medical wipes; food service wipers; clothing articles; pouches, and so forth. In one particular embodiment, for example, a thermochromic nonwoven web formed according to the present invention may be used to form a mitt wipe, such as described in U.S. Pat. No. 5,649,336 to Finch, et al. or U.S. Pat. No. 5,616,201 to Finch. et al., which are incorporated herein in their entirety by reference thereto for all purposes. In another embodiment, the thermochromic nonwoven web may be used to form a wet wipe, such as described in U.S. Pat. No. 6,440,437 to Krzysik, et al.; U.S. Pat. No. 6,028,018 to Amundson, et al.; U.S. Pat. No. 5,888,524 to Cole; U.S. Pat. No. 5,667,635 to Win, et al.; and U.S. Pat. No. 5,540,332 to Kopacz, et al., which are incorporated herein in their entirety by reference thereto for all purposes. When used in an absorbent article, the thermochromic material may undergo a color change at the temperature of a fluid that contacts the article, such as a bodily fluid (e.g., about 38° C.) or saturant solution. This may provide a visual indication of whether the article is wet.

Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core. In one embodiment, for example, a thermochromic film or nonwoven web may be used to form an outer cover of an absorbent article. The thermochromic material may also be used in an elastomeric composite material or layer in various components of the absorbent article, such as side barriers, elastomeric diaper ears, waist bands and other components of disposable, absorbent products. Examples of such elastomeric composite materials may include a continuous filament stretch bonded laminate (CFSBL), a vertical filament laminate (VFL), neck-bonded-laminate (NBL), a stretch-bonded-laminate (SBL), a necked-stretch bonded laminate (NSBL) or a necked-thermal laminate, etc. Exemplary CFSBL, NBL, SBL, and NSBL materials are described in U.S. Pat. Nos. 5,226,992, 4,981,747, 4,965,122, 5,336,545, 5,385,775, 5,414,470, 4,720,415, 4,789,699, 4,781,966, 4,657,802, 4,652,487, 4,655,760, 5,116,662 and 5,114,781, and 6,323,389, all of which are incorporated herein in their entirety by reference thereto for all purposes. Exemplary VFL materials are described in U.S. Patent Application Publication No. 2002/0104608 to Welch, et al., which is incorporated herein in its entirety by reference thereto for all purposes. Still other suitable laminate materials are described in U.S. Pat. No. 6,680,265 to Smith, et al.; U.S. Pat. No. 5,385,775 to Wright; and U.S. Pat. No. 4,720,415 to Vander Wielen, et al., which are incorporated herein in their entirety by reference thereto for all purposes.

Section III—Examples

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

The thermochromic material (e.g., film or nonwoven web) may also be used to form a garment or a protective article. Although the garment can have either a double or multiple layers, typically the garment is likely to be fashioned as a single layer article. When fashioned into the form of a cover, blanket, or pouch that may be used for wrapping or containing a heating pad or pack that provides heat to a user, the thermochromic film or nonwoven web may alert a user to the level of heat present. In such embodiments, the pouch or even as a blanket may undergo a color change upon heating and alert the user that the pad is performing properly.

As stated above, the thermochromic material of the present invention undergoes a color change at an activation temperature. In some cases, the activation temperature is at or near body temperature so that contact with skin or bodily fluids causes the thermochromic material to change color. This color change may provide information (e.g., the presence of overheating) or simply an aesthetically-pleasing appearance to a user. In alternative embodiments, the activation temperature is achieved in the absence of external heat, such as provided by bodily fluids, but instead achieved through heat generated by the thermochromic material itself (i.e., internal heat). For example, stretching, extending, and/or otherwise deforming a nonwoven web generally causes the fibers of the web to rub against each other. When the fibers are incorporated with a thermochromic substance, the present inventors have discovered that the frictional forces created by this "fiber-to-fiber" contact may actually heat the thermochromic substance to its activation temperature, thereby causing the desired color change.

Regardless of the manner in which the temperature increase is actuated, the color change is normally stark and highly visible. For instance, the gray-level value of the original color (prior to activation) may differ from the gray-level value of the changed color (after activation) to a certain degree, such as about 45 or greater on an 8-bit scale of 0-255 (where 0 represents black and 255 represents white). Gray-level values may be determined using a Quantimet 600 Image Analysis System (Leica, Inc., Cambridge, UK) containing software (QWIN Version 1.06A). A control or "blank" white-level may be set using undeveloped Polaroid photographic film. The original color may then be measured for its gray-level value, followed by the same measurement of the changed color. The routine may be programmed to automatically calculate the gray-level value of the colors.

EXAMPLE 1

The ability to form a thermochromic spunbond web in accordance with the present invention was demonstrated. Specifically, 50 grams of a thermochromic masterbatch polypropylene resin was obtained from Matsui International Co., Inc. under the designation Chromicolor® (Blue type #37). The masterbatch was blended with 950 grams of Exxon 3155 polypropylene in a 5-gallon bucket (5 wt. % colorant). The blend was melt-extruded to form fibers under the following conditions:
  Spin pump temp=460° F.;
  Spin pump speed=30.7 rpm;
  Screw zone temp.=469° F.;
  Extruder zone 1=460° F., zone 2=460° F., zone 3=388° F.;
  Pack pressure=130 psi; and
  Residence time for the melt of 10-15 minutes.

Warming of the fibers with either a human hand, warm water or hot air gun caused a blue to white color change. The color change was reversible upon cooling.

EXAMPLE 2

The ability to form a thermochromic spunbond web in accordance with the present invention was demonstrated. Specifically, 35 grams of two different thermochromic masterbatch polypropylene resins were obtained from Matsui International Co., Inc. under the designation Chromicolor® (Blue type #37 and Red type #37). The thermochromic resins were blended with 930 grams of Exxon 3155 polypropylene in a 5-gallon bucket (7 wt. % colorant). The blend was melt-extruded to form fibers as described in Example 1. Warming of the fibers with either a human hand, warm water or hot air gun caused a purple to yellow color change. The color change was reversible upon cooling.

EXAMPLE 3

The ability to form a thermochromic spunbond web in accordance with the present invention was demonstrated. Specifically, 35 grams of a thermochromic masterbatch polypropylene resin was obtained from Matsui International Co., Inc. under the designation Chromicolor® (Blue type #37). The resin was blended with 3 grams of green pigment, and then blended with 463 grams of Exxon 3155 polypropylene in a 5-gallon bucket. The blend was melt-extruded to form fibers as described in Example 1. Warming of the fibers with either a human hand, warm water or hot air gun caused a purple to green color change. The color change was reversible upon cooling.

EXAMPLE 4

The ability to form a thermochromic spunbond web in accordance with the present invention was demonstrated. Specifically, 35 grams of a thermochromic masterbatch polypropylene resin was obtained from Matsui International Co., Inc. under the designation Chromicolor® (Red type #37). The resin was blended with 465 grams of Exxon 3155 polypropylene in a 5-gallon bucket. The blend was melt-extruded to form fibers as described in Example 1. Warming of the fibers with either a human hand, warm water or hot air gun caused a red to yellow color change. The color change was reversible upon cooling.

EXAMPLE 5

The ability to form a thermochromic spunbond web in accordance with the present invention was demonstrated. Specifically, 35 grams of a thermochromic masterbatch polypropylene resin was obtained from Matsui International Co., Inc. under the designation Chromicolore (Red type #37). The resin was blended with 3 grams of green pigment, and then blended with 465 grams of Exxon 3155 polypropylene in a 5-gallon bucket. The blend was melt-extruded to form fibers as described in Example 1. Warming of the fibers with either a human hand, warm water or hot air gun caused a purple/brown to green color change. The color change was reversible upon cooling.

EXAMPLE 6

Fibers were formed as described in Example 2, and then held in a bundle (approximately 20 in a bundle) and stretched about 50% beyond their original length. The stretching caused a vivid purple to green color change. The fibers on stranding returned their purple color.

EXAMPLE 7

Fibers were formed as described in Example 4, and then held in a bundle (approximately 20 in a bundle) and stretched about 50% beyond their original length. The stretching caused a vivid red to yellow color change. The fibers on stranding returned their purple color.

EXAMPLE 8

The fibers of Example 5 were cut and thermally bonded using a Carver hot plate (Carver Lab Press, model 2518, from Fred Carver Inc. of Menomenee Falls, Wis.). The press used steel plates with grooves or protruding lines to melt bond specific areas of the mat to form a nonwoven web. The fibers were exposed to the hot plates (295° F.) for 1 minute or less. Pouches were then made by folding over a sheet of the nonwoven web and melt welding (Impulse Sealer model 210-8E, Clamco Corporation, Cleveland Ohio) the sides together, leaving the forth side open. A heat pack (HOTHAND-2 hand warmers, Heatmax Inc., Dalton Ga.) was then placed in the pouch. This resulted in a color change from purple to green.

EXAMPLE 9

The fibers of Example 2 were cut and thermally bonded using a Carver hot plate (Carver Lab Press, model 2518, from Fred Carver Inc. of Menomenee Falls, Wis.). The press used steel plates with grooves or protruding lines to melt bond specific areas of the mat to form a nonwoven web. The fibers were exposed to the hot plates (295° F.) for 1 minute or less. Pouches were then made by folding over a sheet of the nonwoven web and melt welding (Impulse Sealer model 210-8E, Clamco Corporation, Cleveland Ohio) the sides together, leaving the forth side open. A heat pack (HOTHAND-2 hand warmers, Heatmax Inc., Dalton Ga.) was then placed in the pouch. This resulted in a color change from red to yellow.

EXAMPLE 10

The fibers of Example 1 were cut and thermally bonded using a Carver hot plate (Carver Lab Press, model 2518, from Fred Carver Inc. of Menomenee Falls, Wis.). The press used steel plates with grooves or protruding lines to melt bond specific areas of the mat to form a nonwoven web. The fibers were exposed to the hot plates (295° F.) for 1 minute or less. A small rectangle (2"×4") of the nonwoven web was then placed between the outer spunbond layer and the film layer on the front panel of the HUGGIES® Ultra plus diaper (Kimberly-Clark Corporation, Neenah Wis.). When water at body core temperature (38° C.) was poured into the inside of the diaper, the nonwoven web changed color in less than 1 minute. The color persisted for 20 minutes due in part to the latent heat of water and the insulation properties of the diaper components.

EXAMPLE 11

The fibers of Example 1 were cut and thermally bonded using a Carver hot plate (Carver Lab Press, model 2518, from Fred Carver Inc. of Menomenee Falls, Wis.). The press used steel plates with grooves or protruding lines to melt bond specific areas of the mat to form a nonwoven web. The fibers were exposed to the hot plates (295° F.) for 1 minute or less. A finger brush was made by heat sealing (impulse sealer) two sheets of the nonwoven web together on three sides to form a finger glove shape. Upon exposure to the temperature of the oral cavity, the finger brush changed color over time.

EXAMPLE 12

The fibers of Example 5 were cut and thermally bonded using a Carver hot plate (Carver Lab Press, model 2518, from Fred Carver Inc. of Menomenee Falls, Wis.). The press used steel plates with grooves or protruding lines to melt bond specific areas of the mat to form a nonwoven web. The fibers were exposed to the hot plates (295° F.) for 1 minute or less. The nonwoven web was wrapped around a coffee cup filled with warm water, which caused a color change.

EXAMPLE 13

The ability to form a thermochromic meltblown web in accordance with the present invention was demonstrated. Specifically, 10 pounds of a thermochromic masterbatch polypropylene resin was obtained from Matsui International Co., Inc. under the designation Chromicolor® (Type #27, temperature transition 33° C.). The masterbatch was blended for 10 minutes with 40 pounds of Exxon PF015 polypropylene using a cement mixer. The mixture was then emptied into a bucket (55 gallons) and fed to an extruder under the following conditions:
  Extruder melt temperature=459° F.;
  Melt pressure=347 psi;
  Spin pump pressure=1027 psi;
  Spin pump speed=12 rpm;
  Die melt temp=491° F./523° F.;
  Die melt pressure=48/110 psi;
  Die height=12 inches;
  Die angle=45°; and
  Extruder zone 1=260° F., zone 2=370° F., zone 3=460° F., zone 4=500° F., zone 5=600° F.

The resulting meltblown web had a basis weight of 83 grams per square meter. Warming of the web caused a green to orange color change. The color change was reversible upon cooling.

EXAMPLE 14

The ability to form a thermochromic coform web in accordance with the present invention was demonstrated. Specifically, 10 pounds of a thermochromic masterbatch polypropylene resin was obtained from Matsui International Co., Inc. under the designation Chromicolor® (Type #27, temperature transition 33° C.). The masterbatch was blended for 10 minutes with 40 pounds of Exxon PF015 polypropylene using a cement mixer. The mixture was then emptied into a bucket (55 gallons) and fed to an extruder under the conditions of Example 13. Pulp fibers were also entrained into the extruder (405 Weyerhouser, picker rpm 2650) to form a coform web having a basis weight of 132 grams per square meter and containing 30 wt. % pulp fibers and 70 wt. % polypropylene fibers. The coform web was cut into 7.2×8 inch samples. The samples were exposed to bare hands and lukewarm water (28° C.). The samples changed color upon contact with the hand after 10 to 20 seconds, whereas the water caused the fabric to instantly change color. Coform web samples were also doubled over and cut into mitt glove shapes using an ultrasonic knitting machine (Model FS-90, Branson Ultrasonics Corp., Danbury, Conn.). This produced a wash mitt similar in shape to the current HUGGIES® disposable mitts with body wash. The mitts were placed on the hand causing a color change to occur where the hand surface was in contact with the glove.

EXAMPLE 15

The ability to form a thermochromic coform web in accordance with the present invention was demonstrated. Specifically, 10 pounds of a thermochromic masterbatch polypropylene resin was obtained from Matsui International Co., Inc. under the designation Chromicolor® (Type #27, temperature transition 33° C.). The masterbatch was blended for 10 minutes with 40 pounds of Exxon PF015 polypropylene using a cement mixer. The mixture was then emptied into a bucket (55 gallons) and fed to an extruder under the conditions of Example 13. Pulp fibers were also entrained into the extruder (405 Weyerhouser, picker rpm 2650) to form a coform web having a basis weight of 66 grams per square meter and containing 30 wt. % pulp fibers and 70 wt. % polypropylene fibers. The coform web was then cut into 7.2×8 inch samples and exposed to both hand temperature and lukewarm (28° C.) bath water. The cloth-like shapes changed color in less than 10 seconds when a hand was placed on them. Also, when the wash cloth was placed in the water, it changed color instantly. Both samples recovered their original color on returning to ambient temperature.

EXAMPLE 16

The ability to form a thermochromic coform web in accordance with the present invention was demonstrated. Specifically, 10 pounds of a thermochromic masterbatch polypropylene resin was obtained from Matsui International Co., Inc. under the designation Chromicolor® (Type #27, temperature transition 33° C.). The masterbatch was blended for 10 minutes with 40 pounds of Exxon PF015 polypropylene using a cement mixer. The mixture was then emptied into a bucket (55 gallons) and fed to an extruder under the conditions of Example 13. Pulp fibers were also entrained into the extruder (405 Weyerhouser, picker rpm 2650) to form a coform web having a basis weight of 176 grams per square meter and containing 50 wt. % pulp fibers and 50 wt. % polypropylene fibers. Warming of the web caused a green to orange color change. The color change was reversible upon cooling.

EXAMPLE 17

The ability to form a thermochromic meltblown web in accordance with the present invention was demonstrated.

Specifically, 10 pounds of a thermochromic masterbatch polypropylene resin was obtained from Matsui International Co., Inc. under the designation Chromicolor® (turquoise blue Type #35, transition temperature of 36° C.). The masterbatch was blended for 10 minutes with 40 pounds of Exxon PF015 polypropylene using a cement mixer. The mixture was then emptied into a bucket (55 gallons) and fed to an extruder under the conditions of Example 13 to form a meltblown web having a basis weight of 83 grams per square meter. Warming of the web caused a blue to colorless change. The color change was reversible upon cooling.

EXAMPLE 18

The ability to form a thermochromic coform web in accordance with the present invention was demonstrated. Specifically, 10 pounds of a thermochromic masterbatch polypropylene resin was obtained from Matsui International Co., Inc. under the designation Chromicolor® (turquoise blue Type #35, transition temperature of 36° C.). The masterbatch was blended for 10 minutes with 40 pounds of Exxon PF015 polypropylene using a cement mixer. The mixture was then emptied into a bucket (55 gallons) and fed to an extruder under the conditions of Example 13. Pulp fibers were also entrained into the extruder (405 Weyerhouser, picker rpm 2650) to form a coform web having a basis weight of 125 grams per square meter and containing 30 wt. % pulp fibers and 70 wt. % polypropylene fibers. The coform web was cut into 7.2×8 inch samples. The samples were exposed to bare hands and lukewarm water (28° C.). The samples changed color upon contact with the hand after 10 to 20 seconds, whereas the water caused the fabric to instantly change color.

EXAMPLE 19

The ability to form a thermochromic coform web in accordance with the present invention was demonstrated. Specifically, 10 pounds of a thermochromic masterbatch polypropylene resin was obtained from Matsui International Co., Inc. under the designation Chromicolor® (turquoise blue Type #35, transition temperature of 36° C.). The masterbatch was blended for 10 minutes with 40 pounds of Exxon PF015 polypropylene using a cement mixer. The mixture was then emptied into a bucket (55 gallons) and fed to an extruder under the conditions of Example 13. Pulp fibers were also entrained into the extruder (405 Weyerhouser, picker rpm 2650) to form a coform web having a basis weight of 132 grams per square meter and containing 70 wt. % pulp fibers and 30 wt. % polypropylene fibers. The coform web was then cut into 7.2×8 inch samples and exposed to both hand temperature and lukewarm (28° C.) bath water. The cloth-like shapes changed color in less than 10 seconds when a hand was placed on them. Also, when the wash cloth was placed in the water, it changed color instantly. Both samples recovered their original color on returning to ambient temperature. Coform web samples were also doubled over and cut into mitt glove shapes using an ultrasonic knitting machine. This produced a wash mitt similar in shape to the current HUGGIES® disposable mitts with body wash. The mitts were placed on the hand causing a color change to occur where the hand surface was in contact with the glove. Upon immersing the mitted hand into water, the area of the mitt in contact with the water changed color instantly. Additional samples of the coform web were thermally point bonded using circular bond points the size of pennies. It was observed that the thinner bond point areas changed color before the unbonded areas.

EXAMPLE 20

The ability to form a thermochromic coform web in accordance with the present invention was demonstrated. Specifically, 10 pounds of a thermochromic masterbatch polypropylene resin was obtained from Matsui International Co., Inc. under the designation Chromicolor® (turquoise blue Type #35, transition temperature of 36° C.). The masterbatch was blended for 10 minutes with 40 pounds of Exxon PF015 polypropylene using a cement mixer. The mixture was then emptied into a bucket (55 gallons) and fed to an extruder under the conditions of Example 13. Pulp fibers were also entrained into the extruder (405 Weyerhouser, picker rpm 2650) to form a coform web having a basis weight of 175 grams per square meter and containing 50 wt. % pulp fibers and 50 wt. % polypropylene fibers. Warming of the web caused a blue to colorless change. The color change was reversible upon cooling.

EXAMPLE 21

The ability to form a thermochromic meltblown web in accordance with the present invention was demonstrated. Specifically, two separate thermochromic batches were formed as described in Examples 13 and 17, identified respectively as batches A and B. Batch A was fed to an extruder A and batch B was fed to an extruder B. The resultant meltblown web (basis weight of 90 grams per square meter) had a two-sided appearance with one side being predominantly blue in color and the opposite side being predominantly green.

EXAMPLE 22

The ability to form a thermochromic coform web in accordance with the present invention was demonstrated. Specifically, two separate thermochromic batches were formed as described in Examples 13 and 17, identified respectively as batches A and B. Batch A was fed to an extruder A and batch B was fed to an extruder B. Pulp fibers were also entrained into each extruder (405 Weyerhouser, picker rpm 2650) to form a coform web having a basis weight of 125 grams per square meter and containing 30 wt. % pulp fibers and 70 wt. % polypropylene fibers. The resultant coform had a two-sided appearance with one side being predominantly blue in color and the opposite side being predominantly green. The coform web was cut into 7.2×8 inch samples. The samples were exposed to bare hands and lukewarm water (28° C.). The samples changed color upon contact with the hand after 10 to 20 seconds, whereas the water caused the fabric to instantly change color.

EXAMPLE 23

The ability to form a thermochromic coform web in accordance with the present invention was demonstrated. Specifically, two separate thermochromic batches were formed as described in Examples 13 and 17, identified respectively as batches A and B. Batch A was fed to an extruder A and batch B was fed to an extruder B. Pulp fibers were also entrained into each extruder (405 Weyerhouser, picker rpm 2650) to form a coform web having a basis weight of 164 grams per square meter and containing 50 wt. % pulp fibers and 50 wt. % polypropylene fibers. The resultant coform had a two-sided appearance with one side being predominantly blue in color and the opposite side being predominantly green. The coform web was then doubled over and cut into mitt glove shapes using an ultrasonic knitting machine. This produced a wash mitt similar in shape to the current HUGGIES® disposable mitts with body wash. The mitts were placed on the hand causing a color change to occur where the hand surface was in contact with the glove. Upon immersing the mitted hand into water, the area of the mitt in contact with the water changed color instantly.

EXAMPLE 24

The ability to form a thermochromic film in accordance with the present invention was demonstrated. Specifically, 10 grams of thermochromic polypropylene pellets were obtained from Matsui International Co. under the designation Chromicolor® (deep blue Type #37). The pellets were melt-pressed at a temperature of 175° C. between two sheets of aluminum foil (Reynolds Wrap™, Alcoa Inc., Richmond, Va.) for 20 to 30 seconds at 1000 psi using a carver hotplate press (Carver Lab Press, model 2518, Fred Carver Inc. of Menomenee Falls, Wis.). The resulting film was circular and blue, and turned colorless (e.g., transparent) when warmed by human hand, warm water, or hot air gun. A pouch was then made from the film by overlaying two layers of the film and then melt sealing their edges with an impulse sealer (Impulse Sealer model 210-8E, Clamco Corporation, Cleveland Ohio). A handwarmer sachet (HOTHAND-2 hand warmers, Heatmax Inc., Dalton Ga.) was then placed inside the pouch. A vivid color change occurred within 30 seconds. Further, small rectangular samples (2"×4") of the film was placed between the spundbond layer and the film layer of a HUGGIES® ultra diaper. Water at body core temperature was then poured into the diaper and the wetness indicator strip observed. Within 20 seconds, the strip started to change color. The area of the strip that changed color was in part dependent on the volume of the warm water, or urine, poured into the diaper.

EXAMPLE 25

The ability to form a thermochromic film in accordance with the present invention was demonstrated. Specifically, 10 grams of thermochromic polypropylene pellets were obtained from Matsui International Co. under the designation Chromicolor® (red Type #37). The pellets were melt-pressed at a temperature of 175° C. between two sheets of aluminum foil (Reynolds Wrap™, Alcoa Inc., Richmond, Va.) for 20 to 30 seconds at 1000 psi using a carver hotplate press (Carver Lab Press, model 2518, Fred Carver Inc. of Menomenee Falls, Wis.). The resulting film was circular and blue, and turned yellow when warmed by human hand, warm water, or hot air gun. A pouch was then made from the film by overlaying two layers of the film and then melt sealing their edges with an impulse sealer (Impulse Sealer model 210-8E, Clamco Corporation, Cleveland Ohio). A handwarmer sachet (HOTHAND-2 hand warmers, Heatmax Inc., Dalton Ga.) was then placed inside the pouch. A vivid color change occurred within 30 seconds. Further, small rectangular samples (2"×4") of the film was placed between the spundbond layer and the film layer of a HUGGIES® ultra diaper. Water at body core temperature was then poured into the diaper and the wetness indicator strip observed. Within 20 seconds, the strip started to change color. The area of the strip that changed color was in part dependent on the volume of the warm water, or urine, poured into the diaper.

EXAMPLE 26

The ability to form a thermochromic film in accordance with the present invention was demonstrated. Specifically, 5 grams of thermochromic polypropylene pellets were obtained from Matsui International Co. under the designation Chromicolor® (red Type #37). Likewise, 5 grams of thermochromic polypropylene pellets were obtained from Matsui International Co. under the designation Chromicolor® (deep blue Type #37). The pellets were spread onto a sheet of aluminum foil to form a circle in which one half of the circle contained the blue pigment pellets and the other half contained the red pigment pellets. The pellets were then melt-pressed as described in Example 24 to form a film circle in which one half was blue and the other half was red. The boundary area where the two colors mixed was purple/brown. When the film contacted a human hand, warm water, or hot air gun, the colors changed. The boundary section of the two colors turned from purple/brown to green followed by yellow. This color transformation is explained by the purple/brown being generated by simple mixing of the red and blue primary colors. This turned green due to the red pigment changing to yellow, but as it was still mixed with blue the resultant color is green (Blue+yellow=green). With time, the blue turned colorless due to the action of heat resulting in that section of the film turning yellow.

EXAMPLE 27

The ability to form a thermochromic film in accordance with the present invention was demonstrated. Specifically, 5 grams of thermochromic polypropylene pellets were obtained from Matsui International Co. under the designation Chromicolor® (red Type #37). Likewise, 5 grams of thermochromic polypropylene pellets were obtained from Matsui International Co. under the designation Chromicolor® (deep blue Type #37). The pellets were randomly spread onto a sheet of aluminum foil to form a circle. The pellets were then melt-pressed as described in Example 24. This formed as film having a "tie-dyed" appearance. When warmed with a human hand, warm water, or hot air gun, the sections of the film having one pigment (e.g., red) changed color before the other section (e.g., blue) changed color. This was due to the red pigment having a lower temperature color change than that of the blue pigment.

EXAMPLE 28

The ability to form "cold sensing" articles comprising a thermochromic spunbond web in accordance with the present invention was demonstrated. Specifically, 35 grams of a thermochromic masterbatch polypropylene resin was obtained from Matsui International Co., Inc. under the designation Chromicolor® (Green type #15). The thermochromic resin was blended with 930 grams of Exxon 3155 polypropylene in a 5-gallon bucket (7 wt. % colorant). The blend was melt-extruded to form fibers as described in Example 1. Cooling of the fibers with cold water caused a colorless to green color change. The color change was reversible upon heating.

EXAMPLE 29

The ability to form a thermochromic spunbond web in accordance with the present invention was demonstrated. Specifically, 35 grams of thermochromic masterbatch polypropylene resin was obtained from Matsui International Co., Inc. under the designation Chromicolor® (Fast Black type #5). The thermochromic resin was blended with 930 grams of Exxon 3155 polypropylene in a 5-gallon bucket (7 wt. % colorant). The blend was melt-extruded to form fibers as described in Example 1. Cooling of the fibers with ice or dry ice caused a colorless to black color change. The color change was reversible upon heating.

EXAMPLE 30

Layered or zoned sheet substrates may be prepared by placing thermochromic spunbond or meltblown fabrics on top of each other, or in strips, before thermal bonding. This will generate substrates with multiple colors and also afford substrates with zones or areas with different temperature sensitivity. Thus, certain zones would change color at temperature A and other areas would change color at a higher temperature.

EXAMPLE 31

To test samples of the thermochromic polymers, a selection of Chromicolor® polypropylene concentrate (Matsui International Co.) was blended with meltblown grade polypropylene pellets in a mixer for about 10 minutes, and then fed into an extruder intake hopper of a coform line unit. In a first sample, Batch A, a combination of Chromicolor® green type #127 (10 lbs., transition temperature=33° C., lot #N30510034) and Exxon PF 015 (40 lbs.) was used to make a roll of 83 grm meltblown fabric. In a second sample, Batch B, a Chromicolor® turquoise blue type #35 (10 lbs., transition temperature=36° C. lot #N3051003) and Exxon PF015 (40 lbs.) were made into a roll of 83 gsm meltblown. The color of the meltblown polymer of Batch A changed from green to orange upon exposure to a heat source. The color of the meltblown polymer of Batch B changed from turquoise blue to clear colorless upon exposure to a heat source. The polymer mixtures from both batches were entrained with cellulose fibers during extrusion to create various base sheet coform fabrics: a) 132 gsm having 30% pulp fiber and 70% polypropylene fiber; b) 66 gsm having 70% pulp fiber and 30% polypropylene fiber (which has a more wash-cloth feel); and c) 176 gsm having 50% pulp fibers and 50% polypropylene.

A 66 gsm coform fabric sample made from Batch A, as well as a 132 gsm coform fabric sample made from Batch B, each was selected to create proof-of-concept garments for babies, including shirts and hats. Each material was cut and folded over, and a pattern was drawn on one side. A Branson LF90 ultrasonic bonder was used to cut and sew the garments along the pattern. Hats were made using a sewing technique that created a done. After the garments were completed, they were photographed and then exposed to a heat source for about one minute. The garment that was made from the green-colored material changed to a crème-orange color, while the garment that was made from the blue-colored material changed to completely white. The color change observed was rapid. Once the heat source was removed, the garments turned back to their original colors over a period of about several minutes (e.g., ~2-4 minutes). Although this example embodies a single color change in the garments, it is envisioned that other additional or combinations of thermochromic resins can be incorporated into a nonwoven fabric for the garments or protective articles for an indicator of being "warm enough," "too warm," or "too cool," to be present in the same garment or article. In other words, multiple functions to communicate various states of temperature homeostasis or non-stasis on or near a user's body.

While the invention has been described in general and in detail with respect to examples of specific embodiments thereof, it will be appreciated that those skilled in the art, upon attaining an understanding of the foregoing, may readily conceive of modifications to, variations of, and equivalents to these embodiments. Accordingly, the scope of the present invention should be assessed as that of the appended claims and any equivalents thereto.

We claim:

1. A method of sensing and visually indicating relative body temperature, the method comprises:
   a) providing a body covering that is fabricated at least in part with a melt-extrudable polymer material and at least two thermochromic colorants pre-blended with a semi-crystalline carrier resin, wherein the thermochromic colorants and the carrier resin are contained within a matrix of said polymeric material, said thermochromic colorants including a proton-accepting chromogen and a solvent, said solvent having a melting point that controls relative temperature at which the chromogen will change color, wherein the thermochromic colorants are visually reactive at a certain temperature or temperature range, and at least one of said thermochromic colorants is sensitive to a temperature within a range from about 32° C. to about 38° C.;
   b) applying said body covering to a portion of a heat-emanating body, and
   c) monitoring for an observable change in color of the body covering.

2. The method according to claim 1, wherein said method further comprises correlating said color change with a temperature range.

3. The method according to claim 1, wherein said body covering is either a garment or protective article.

4. The method according to claim 1, wherein said thermochromic colorants are present in combination with a non-temperature sensitive colorant, which serves as a reference.

5. The method according to claim 1, wherein said observable color change exhibits a ΔE value greater than three (>3).

6. The method according to claim 1, wherein said observable color change exhibits a ΔE value greater or equal to five (≧5).

7. The method according to claim 1, wherein said observable color change exhibits a ΔE value greater or equal to twenty (≧20).

8. The method of claim 1, wherein the semi-crystalline carrier resin includes an ethylene-based polymer, propylene-based polymer, or a combination thereof.

9. A method for instructing a caregiver on the use of a temperature monitoring device, the method comprising:
   a) providing a body covering made at least in part with a melt-extrudable polymeric material a thermochromic substance pre-blended with a semi-crystalline carrier resin, wherein the thermochromic substance that includes a proton-accepting chromogen and a solvent, and which is not of a chloresteric liquid crystal, wherein said thermochromic substance and said carrier resin are contained within a matrix of said polymeric material and wherein said thermochromic substance communicates a visually detectable signal at a predetermined temperature or temperature range, and exhibits an observable color change of a ΔE value greater than three (>3);
   b) contacting said body covering to a warm-blooded body;
   c) monitoring a visual change in said body covering; and
   d) providing an instruction to said caregiver about said temperature monitoring device.

10. The method of claim 9, wherein the semi-crystalline carrier resin includes an ethylene-based polymer, propylene-based polymer, or a combination thereof.

11. A device for monitoring relative body temperature by non-electronic visual indication, said device being part of a body covering that is at least partially made with a melt-extrudable polymeric material, said device containing a temperature-sensitive colorant and a semi-crystalline carrier resin contained within a matrix of said polymer material, wherein said temperature sensitive colorant includes a proton-accepting chromogen and a solvent, and said temperature-sensitive colorant manifests a color change at a predetermined temperature or temperature range that is from about 34° C. to about 38° C.

12. The device according to claim 11, wherein said temperature-sensitive colorant is present in combination with a non-temperature sensitive colorant.

13. The device according to claim 11 wherein said polymeric material manifests a visually observable color change with a change of body temperature.

14. The device according to claim 11, wherein said device is adapted to monitor a change in relative temperature between a body core and body extremities of a warm-blooded animal.

15. The device according to claim 11, wherein said temperature range is within the body temperature range of a living mammalian animal, and said color change exhibits a $\Delta E$ value greater than five (>5).

16. The device of claim 11, wherein the semi-crystalline carrier resin includes an ethylene-based polymer, propylene-based polymer, or a combination thereof.

17. The device according to claim 11, wherein said body covering is either a garment or a protective article.

18. The device according to claim 17, wherein said device includes at least two temperature-sensitive colorants, each temperature-sensitive colorant being visually reactive within a particular temperature range, and exhibits an optical color change of a $\Delta E$ value greater or equal to fifteen ($\geq 15$).

19. An article of manufacture comprising: a body covering that is made in part with a melt-extrudable polymeric material, the covering containing a first thermochromic colorant sensitive to a temperature range from about 30° C. to about 42° C., a second thermochromic colorant sensitive to low temperature range from about −20° C. to about 10° C., and a semi-crystalline carrier resin contained within a matrix of said polymeric material, at least one of the colorants being a thermochromic colorant that includes a proton-accepting chromogen and a solvent, and manifests a color change when exposed to a predetermined temperature or temperature range.

20. The article of manufacture according to claim 19, wherein said article manifests a visually observable indication of relative body temperature for monitoring either poor circulation, relative levels of hypothermia or hyperthermia.

21. The article of manufacture according to claim 19, wherein said article has at least two layers of dissimilar temperature sensitive colorants that are tunable for dissimilar temperature sensing values under either cold or hot conditions.

22. The article of manufacture according to claim 19, wherein said article comprises either a woven or nonwoven fabric, or combinations thereof.

23. The article of manufacture according to claim 19, wherein said article comprises either a stretchable or non-stretchable film, or combinations thereof.

24. The article of manufacture according to claim 19, wherein said article comprises temperature-sensing colorants over at least 10% of a body contacting area.

25. The article of manufacture according to claim 19, wherein said garment or protective article comprises unbonded fabric and either melt or ultrasonic bonded areas, said bonded areas change color as a function of sensing a difference in temperature relative to the rest of said unbonded fabric.

26. The article of manufacture according to claim 19, wherein said article of manufacture exhibits a visual contrast of a $\Delta E$ value of greater than or equal to 10.

27. The article of manufacture of claim 19, wherein the semi-crystalline carrier resin includes an ethylene-based polymer, propylene-based polymer, or a combination thereof.

28. The article of manufacture according to claim 19, wherein said body covering is a garment or a protective article.

29. The article of manufacture according to claim 28, wherein said article when worn by or applied to a heat-emanating body of an animal communicates a relative temperature difference between a core body and body extremities.

* * * * *